(12) United States Patent
Martin

(10) Patent No.: US 10,398,582 B2
(45) Date of Patent: Sep. 3, 2019

(54) INTERGLUTEAL HEMORRHOID PAD

(71) Applicant: Theodore F. Martin, Southborough, MA (US)

(72) Inventor: Theodore F. Martin, Southborough, MA (US)

(73) Assignee: HR BRANDS LLC, Southborough, MA (US)

( * ) Notice: Subject to any disclaimer, the term of this patent is extended or adjusted under 35 U.S.C. 154(b) by 1054 days.

(21) Appl. No.: 14/730,137

(22) Filed: Jun. 3, 2015

(65) Prior Publication Data

US 2016/0354221 A1 Dec. 8, 2016

(51) Int. Cl.
*A61F 5/00* (2006.01)

(52) U.S. Cl.
CPC .................................. *A61F 5/0093* (2013.01)

(58) Field of Classification Search
CPC .......... A61F 5/0093; A61F 2013/15113; A61F 13/15; A61F 2013/15121; A61F 2013/1513; A61F 2013/15138; A61F 2013/1546

See application file for complete search history.

(56) References Cited

U.S. PATENT DOCUMENTS

| | | | |
|---|---|---|---|
| 2,128,670 A * | 8/1938 | Bolder | A61F 5/0093 128/98.1 |
| 4,938,221 A | 7/1990 | Tuffel | |
| 5,707,645 A | 1/1998 | Wierson | |
| 6,018,093 A | 1/2000 | Roe | |
| 6,202,234 B1 * | 3/2001 | Henderson | A47C 7/021 5/653 |
| 6,716,229 B2 | 4/2004 | Toth | |
| 6,913,573 B1 | 7/2005 | Viscomi | |
| 8,123,760 B2 | 2/2012 | Blurton | |
| 8,596,280 B2 | 12/2013 | Blurton | |
| 2001/0003157 A1 * | 6/2001 | Toth | A61F 5/0093 606/197 |
| 2005/0182376 A1 | 8/2005 | Fleming | |
| 2009/0088706 A1 | 4/2009 | Tai | |

FOREIGN PATENT DOCUMENTS

GB 191315173 A * 11/1913 ........... A61F 5/0093

* cited by examiner

*Primary Examiner* — Kari K Rodriquez
(74) *Attorney, Agent, or Firm* — Bycer Law, PLC; Matthew L. Bycer

(57) ABSTRACT

A hemorrhoid relief product that provides an intergluteal spacer for the selective pressure adjustment, relief, and/or pressure application to portions of hemorrhoidal tissue in and or around the perianal. The product optionally includes adhesive to secure the device in place. The product includes a cavity for positioning over hemorrhoidal tissue to provide pressure adjustment, and may also include at least one nub for selectively applying and/or adjusting pressure to areas. The product may include a trapezoidal, or other, cross-section for easier fit, as well as a split end for adherence to multiple gluteal cheeks and anatomy in the relevant area.

16 Claims, 17 Drawing Sheets

INTERGLUTEAL HEMORRHOID PAD

FIELD OF THE INVENTION

The present invention relates to hemorrhoid relief devices. More particularly, the present invention relates to exterior intergluteal pads positioned to adjust pressure(s) associated with internal and external hemorrhoids.

BACKGROUND OF THE INVENTION

Hemorrhoids, and varicose veins, create perianal discomfort in a large population of people. Discomfort is caused by numerous issues associated with the varicosities, such as, swelling, prolapse of sensitive anal tissue, drying of prolapsed tissue, localized trauma, chafing of external hemorrhoids, sensitive prolapsed internal hemorrhoids, thrombosis, or a persistent bleeding/healing cycle. Pressures and rubbing in these areas can cause a feeling of discomfort, as well as cause trauma which can exacerbate conditions, delays recovery and activate nerve cells that indicate pain and injury.

Traditional approaches to hemorrhoid relief have included flat medicated pads, suppositories, and/or topical ointments. None of these products addresses the anatomical reasons for hemorrhoid discomfort. Hemorrhoidal sitting alters the anatomy of the anal area, and can worsen hemorrhoid symptoms by exacerbating prolapse of internal and external hemorrhoids. When a patient or user exhibiting the symptoms of hemorrhoids takes as sitting position, venous pressures increase, which can cause or exacerbate hemorrhoids.

It is therefore an object of the present invention to provide a pad for the relief of discomfort associated with hemorrhoids.

It is a further object of the present invention to provide external application of a spacer for the relief of pressure associated with swollen varicose anal veins.

It is yet another object of the present invention to provide perianal treatment post-operative or post-trauma.

It is still yet another object of the present invention to provide a pad for application of therapeutic medications perianally.

It is another object of the present invention to selectively apply pressure to perianal issue.

SUMMARY OF THE INVENTION

The present invention provides relief of hemorrhoid discomfort by making gentle alterations to the perianal, anal, and hemorrhoidal anatomy, as well as the anatomy of the surrounding tissue. Beneficial alterations to the anatomy include gentle separation of the gluteal cheeks, external support of hemorrhoidal tissue with a cradling effect on inflamed or prolapsed or related perianal tissues, while providing absorption. Alternatively, the present invention can include various contours and/or nubs to apply pressure in specific locations in, on-or-around the affected area to provide relief of pain or discomfort and/or manual reduction in prolapse or swelling.

The present invention is intended as a single-use disposable product, and may be sterile. It is preferably composed of malleable, absorbent material, e.g., cotton, polymer, polyester, rayon, cellulose, viscose, wood, rubber, foam, fibers, blend of fibers, etc. The present invention is not meant for internalization into the anorectal canal. The present design can allow for application of accepted hemorrhoidal medications for additive relief via impregnated foam body or body portions.

When an embodiment of the present invention is in use, it is preferably gently inserted between the separated gluteal cheeks providing improved separation and pressure adjustment. The pad surface interfaces with the external anal canal and is contoured to provide support with a pressure level chosen by the user based on positioning of the intergluteal pad in relation to anatomy and any hemorrhoid(s). The interface surface may include cavities or extensions to mate with hemorrhoid anatomies. The interface surface can act as a platform to hold accepted hemorrhoid topical medications. The device is intended to be worn between two and twelve hours.

In one alternative embodiment of the present invention, an intergluteal spacing device allows selective pressure application and pressure relief in and surrounding the anus. The device preferably includes an elongated body to fit within the intergluteal space with a dorsal (or posterior) end (i.e. positioned upwards for a standing individual) and a ventral (or anterior) end (i.e. facing downwards). It is preferred that at least a part of the central portion of the device would be positioned in direct contact with, or opposite, the anus. The central portion would include at least one cavity to provide the pressure relief over an affected area, such as a prolapsed hemorrhoid, or the cavity can extend over the totality of the perianal. The central portion may have one, two, or more cavities to provide place specific pressure relief and/or adjustment in multiple areas. In one preferred embodiment, the device may be in the form of as trapezoid, with the narrow top fitting up against the perianal skin, while the wide bottom faces outward away from the perianal. Alternatively a rectangular shape can be used. The end(s) may terminate in a beveled shape. The device may alternatively include a convex top to provide ease and comfort to the wearer, the top being generally convex or flat with a portion, or portions, concave to provide a cavity or cavities. The concave section may include a wrap-around concavity (including top and sides) covering at least 180 degrees of the midline to provide additional pressure relief opposite the anus.

An adhesive may be used to affix the device onto the skin, so as to prevent movement, trauma, etc. Certain portion, or portions, of the device may include adhesive. In one embodiment, the ends are covered with adhesive. In another embodiment, the anterior end is split in two, to provide adhesive attachment near the perineum, or along the thighs, and the posterior end to be adhered between the gluteal cheeks, or conversely or lacking adhesive.

In an alternative embodiment, the device may include one, or more, nubs arranged to selectively apply and/or relieve pressure on a section in and/or around said anus. The portion facing the skin may be textured to include an array; pattern, or individual nub or nubs.

The invention also contemplates as method for achieving comfort and relief from pain or discomfort associated with the signs and symptoms of hemorrhoids. The method includes applying an intergluteal spacer between the gluteal cheeks with at least one cavity for relative pressure relief upon inflamed perianal tissue. The method may include the step of adhering an adhesive to the skin to secure the spacer in a specific effective location. The method may also include the step of positioning a nub at a specific location to selectively apply pressure upon, near, or opposite the inflamed or prolapsed tissue, and/or to restore normal anatomy. Applying pressure may include repositioning of pressures, tissues, or alleviation pressure on nerves.

BRIEF DESCRIPTION OF THE DRAWINGS

The present invention can be further illustrated through as description of certain embodiments.

DETAILED DESCRIPTION OF PREFERRED EMBODIMENTS

The present invention includes various shapes and features that may be applied to a spacer pad that can be placed between the gluteal cheeks for the relief of pressures and trauma associated with hemorrhoid symptoms. The surface of the spacer should include at least a feature whereby pressure may be adjusted or relieved, such as a cavity or a concave portion. When applied to the skin or over a hemorrhoid, the cavity allows hemorrhoidal, or any select perianal, tissue a low-pressure space to comfortably sit. Alternatively, a convex or flat surface on the device can provide counter-pressure against a prolapsed internal hemorrhoid or external hemorrhoid. In one preferred embodiment of the present invention, the pad is made from cotton blend, whereby the pad structure can be maintained in a predetermined form to maintain its lit while adapted to mate with the skin or a portion of the pad can conform to the body, while the remainder of pad retains its shape. The type of material preferred for the invention is gentle enough to allow the pad to conform to a prolapsed or inflamed tissue, thereby providing support in its current form. The gentle invention structure can push up against inflamed, swollen, or prolapsed tissue, and support the shape of the tissue, reducing pressure on the anatomy. Inflamed exterior hemorrhoids may be similarly supported. The pad is meant for short term relief and/or post-surgery relief.

Figure 1A:
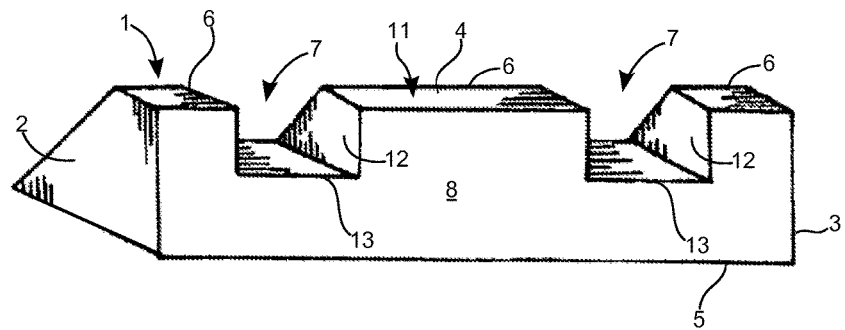
FIG. 1A demonstrates a perspective view of a side of an embodiment of the present invention.
Figure 1B:
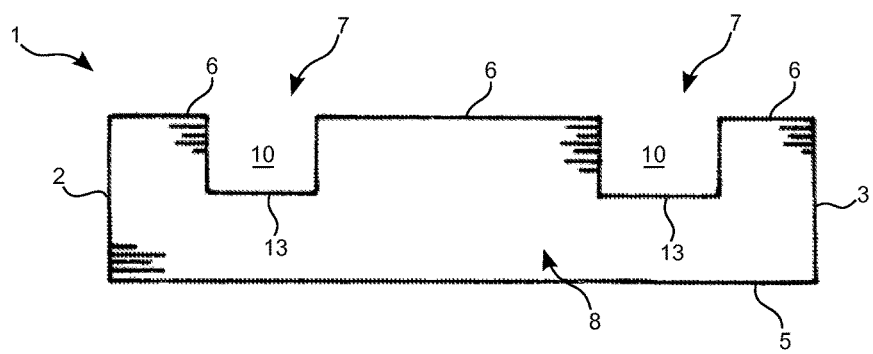
FIG. 1B demonstrates a side view of an embodiment of the present invention.
Figure 1C:
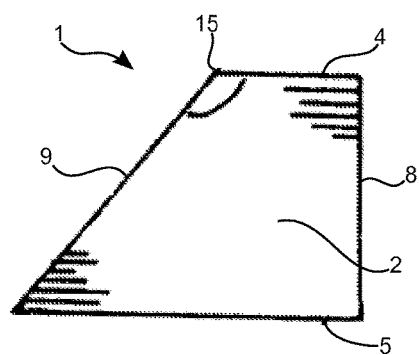
FIG. 1C demonstrates an end view of an embodiment of the present invention.

Referring now to drawings of the preferred embodiments, FIGS. 1A-C demonstrates an embodiment of the present invention. Intergluteal pad 1 has top 4 adapted to contact the human perianal and surrounding skin within the intergluteal space and along the skin surface. Bottom 5 is adapted for outwardly facing, i.e. away from the anus. Left side 8 and right side 9 provide additional optional surface area to contact with the interior of the left and right gluteal cheeks. Intergluteal pad 1 contains an anterior end 2 adapted for facing towards the perineum, and posterior end 3 adapted for facing towards the coccyx. The top may contain features such as the pressure elements 6 and concave spaces 7 which can provide for cavities 10. Top 4 may include an interactive surface 11, which may include an adhesive to affix the pad in place, creams for therapeutic use, nubs, etc.

Therapeutic medications may be impregnated into pressure elements, particularly when such elements are to be positioned to provide pressure on, or for the manual reduction of prolapsed, inflamed, or swollen tissue. Cavities may alternatively be coated with topical medication to allow pressure-relieved prolapsed, inflamed, or swollen tissues to gently receive medication initially, and when prolapsing exaggerates the size of prolapsed tissue or swelling.

Furthermore, the intergluteal pad is preferably comprised of a cotton blend. Alternatively, the pad is made from a firm foam, preferably petroleum based or (synthetic) rubber. In one embodiment, the pad may be impregnated with a liquid for the application of therapeutic treatments, such as pain relief, steroids, non-steroidal anti-inflammatory, clotting agent, hemostatic lubricant, anti-biotic ointment, etc. The invention may be used to treat damaged tissue in the perianal area, or used for post-operative treatment. After surgery, the invention may be used to secure, support, or treat damaged/healing tissues, or may be used as a means for post-operative manipulation of part or all of the perianal tissues. The invention can be used to treat or support tissue with stitches, such as post episiotomy, or used post child-birth. The invention may be used to treat damage, trauma, swelling or irritation caused by Crohn's disease, perianal fistula, or any fissure or abscess. The invention may be used to treat any perianal diseased state or perianal tissues.

When adhesives are used in this embodiments or others, common mild adhesives known in the art are contemplated as best mode for the temporary affixing of a product to human skin, preferably an adhesive more mild than a typical bandage.

Cavity 10 may include sidewall 12, which may be flat, and may be fared at a right angle from surface 11. Cavity defines a specific volume of space for controlled pressure adjustment, being further defined by cavity base 13. In this embodiment, skies of cavity 10 remain open to allow the user's gluteal cheeks to enclose the cavity space so to provide relaxed pressure relief to an anal area opposite the cavity base 13.

Intergluteal pad 1 may also include sides 8 and 9 with alternating angles to better provide for fit and/or comfort when applied. While hemorrhoids can come in any position 360 degrees surrounding the perianal, most common hemorrhoids are left lateral, right anterior and right posterior. In the embodiment in FIGS. 1A-C, left side 8 meets top 4 surface 11 at a right angle, while right side 9 meets top 4 at an obtuse angle 15. Preferably the angle is approximately one hundred thirty-five degrees, but may vary from ninety to one hundred-fifty degrees. In this instance, top 4 is narrow while bottom 5 is wider, to provide for ease of fit and better form it between the gluteal cheeks. Partial cross-section is demonstrated as seen in side view 1C. Depending on specific patient condition, intergluteal pad 1 can be flipped one hundred-eighty degrees side-side to make the anterior end posterior and posterior end anterior, while maintaining top in body-facing position.

Figure 2A:
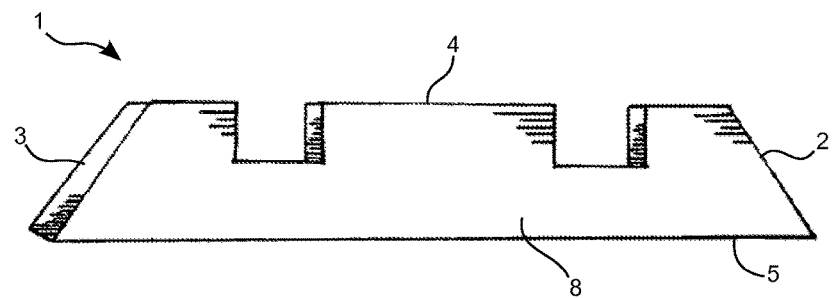
FIG. 2A demonstrates a side view of an embodiment of the present invention.
Figure 2B:
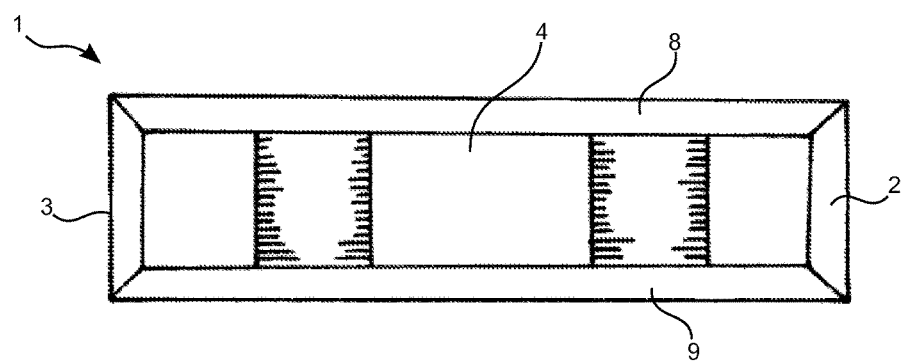
FIG. 2B demonstrates a top view of an embodiment of the present invention.
Figure 2C:
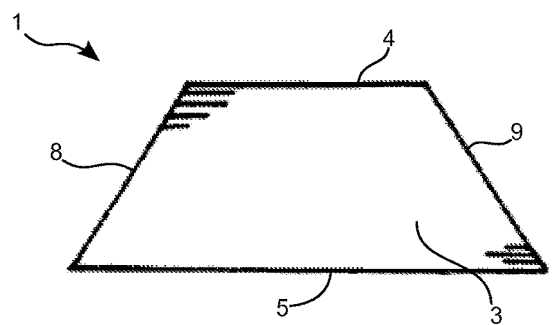
FIG. 2C demonstrates an end view of an embodiment of the present invention.

Referring now to FIGS. 2A-C, an alternative embodiment of the intergluteal pad 1 includes a trapezoidal shape. As seen in FIG. 2C, the pad includes a trapezoidal shape, whereby top 4 leads to sides 8 and 9 at a substantially identical obtuse angle, and sides meet base 5 at a substantially identical acute angle (For the purposes of this specification substantially and substantially identical means+/−5 degrees). Preferably obtuse and acute angles add up to one hundred-eighty degrees, and preferably obtuse angle is between one hundred and one hundred-forty degrees, most preferably one hundred-ten degrees, and acute angles make up the difference to one hundred-eighty degrees. In this manner, the symmetric shape of the pad allows for adjustment, whereby posterior end 3 may be positioned wither posterior or anterior, allowing the pad to be rotated freely. When top 4 includes varied features (described below FIGS. 3-5, etc.), the product can be adjusted as necessary. To provide additional adaptation to the anatomies of the intergluteal area, posterior end 3 and anterior end 2, may also include as gradual obtuse angle off of top 4. This allows liar a more gradual pressure at the ends of the pad when applied and used, especially when the user is sitting down or the gluteal cheeks are otherwise under pressure or alternatively, separated. Adhesives may also be included on sides, such as sides 8 and 9 to secure pad 1 in place.

Figure 3:
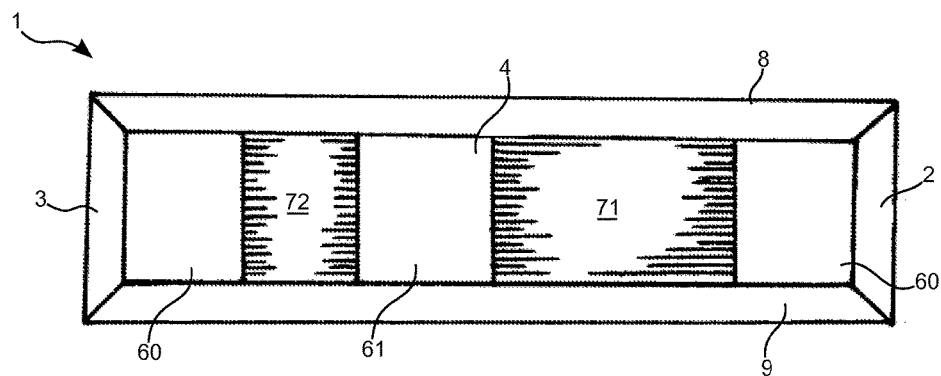
FIG. 3 demonstrates a top view of an alternative embodiment of the present invention.
Figure 4:
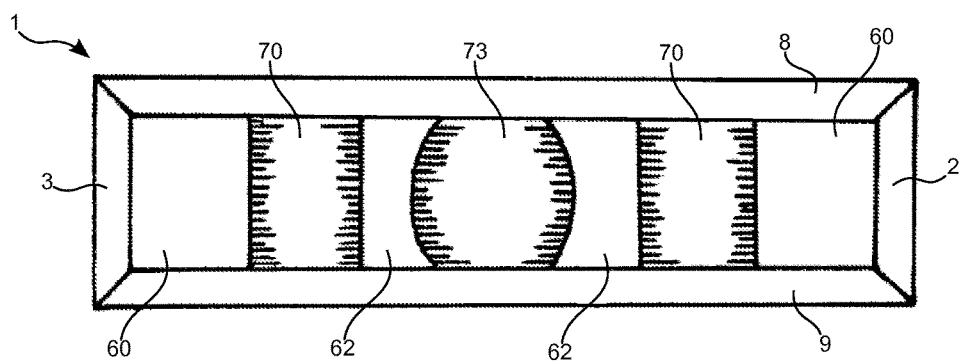
FIG. 4 demonstrates a top view of an alternative embodiment of the present invention.
Figure 5:
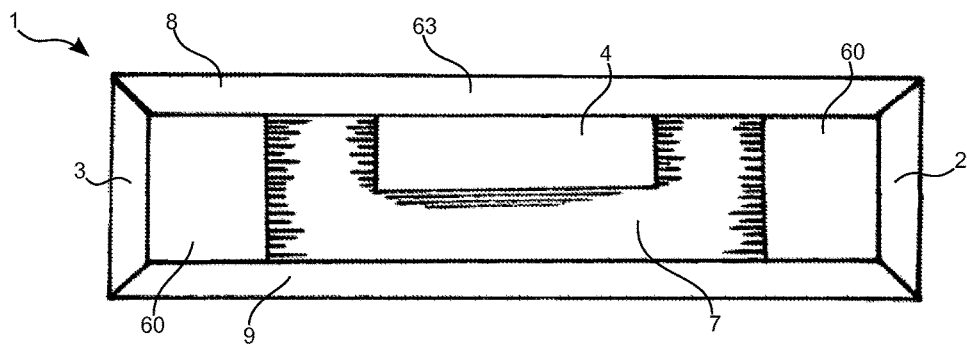
FIG. 5 demonstrates a to view of an alternative embodiment of the present invention.

As shown in FIGS. 3-5, top 4 may include varied features for the preferential and optional positioning of varied pressure adjusting features for application to the hemorrhoidal areas. As seen in FIG. 3, top 4 may include pressure elements 6 in a non-symmetrical fashion. Certain cavities 70 may have varied sizes and/or shapes. For instance cavity 71 is notably larger (by means of lengthening between ends 2 and 3) to provide additional pressure relief to the perianal anterior. Feature 61 may be positioned over a portion of, or the totality of the anus. Feature 61, or any pressure feature 60, 61, 62, 63 et al., may include a varied material that provides extra absorption to collect discharged blood, and/or to provide selective application of pre-impregnated therapeutic solution. Cavity 72 may be positioned above posterior side of the anus, or over specific hemorrhoidal bulges. The device, as always, can be flipped, based on the condition and/or preference of be user.

As seen in FIG. 4, top 4 may include central cavity 73 rounded to better fit the features of the anatomy. In this instance, cavity 73 can be sized for adaptation over the center of the anus, to accommodate/cradle/support bulging of internal prolapsed hemorrhoids. When central cavity 73 is smaller than external hemorrhoids, pressure elements 62 may be positioned over the external hemorrhoids to provide pressure on external hemorrhoidal plexus and/or against the sphincter muscle, and to prevent varicosities from expanding laterally beyond the perianal, or protect any prolapse or swelling tissues from trauma. Further cavities 10 may be provided to allow other hernias or external hemorrhoidal or prolapses space for pressure relief. Alternatively, cavities 10 provide for more flexibility of pressure elements 62 to migrate/bend as needed or forced by the geometry of the area.

As seen in FIG. 5, vertical pressure element 63 can be provided on one side of intergluteal pad 1 to specifically target non-symmetrical, g, left lateral) hemorrhoids that may appear on one side or the other. Concave space 7 provides for pressure relief and to allow additional pressure contact of pressure element 6C. Given the symmetrical shape of sides 8 and 9 and ends 2 and 3, the added benefit contained in this embodiment is the ability to flip the product so as to position the pressure element 63 on either side, as needed. When flipped, posterior end 3 is positioned anteriorly and anterior end 2 is positioned posteriorly.

Figure 6A:
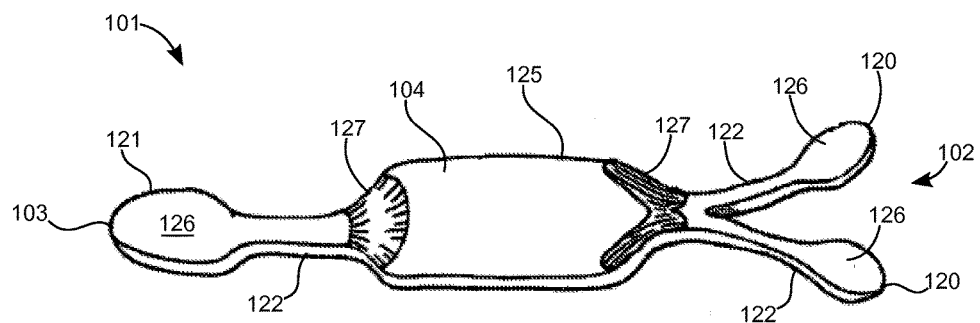
FIG. 6A demonstrates a top view of an embodiment of the present invention.
Figure 6B:
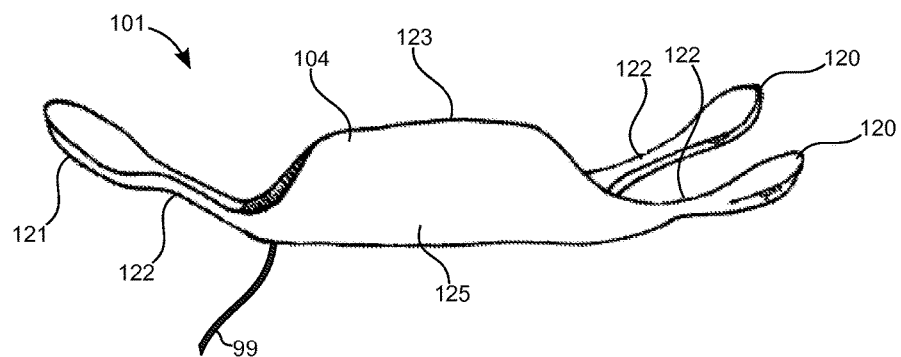
FIG. 6B demonstrates as side view of an embodiment of the present invention.

Referring to FIGS. 6A-B, an alternative embodiment is shown. Intergluteal pad 101 includes body 125 for insertion over the perianal. Contact surface 124 on top 104 may contact the anus, external hemorrhoidal plexus and/or prolapsed hemorrhoids or other hernia external of the patient's body. As seen in FIG. 6B, body may include wedge shape 123 opposite wide base 113 to allow for more comfortable fit between the gluteal cheeks, and well as to provide directed pressure to the perianal. Body 125 meets necks 122 via slopes 127. Slopes allow for additional space between necks 122 and the patient's skin. On anterior end, necks may be preferably bifurcated, terminating in preferably two heads 120. Heads 120 may be affixed to either side of the genitalia and/or the inner thigh of the patient. Heads 120 preferably include adhering surface 126 to affix to the patient and keep the product in place. Adhering surface 126 preferably includes an adhesive to hold pad 101 to patient's skin. Posterior end 103 includes posterior end 121, attached to body 125 via, neck 122. Posterior bead 121 may be affixed between the gluteal cheeks to further secure pad 121. Pad 101 may be flipped, whereby bifurcated neck pads 126 affix to gluteal cheeks, and/or device may include a single neck on either side, or dual necks on both sides.

Preferably, when handle 99 is used in conjunction with the embodiment shown in FIGS. 6A and 6B, handle is positioned at the bottom towards posterior end 103, as shown. However, handle may be affixed to head 121, or heads 120, or otherwise mounted at bottom near anterior end 102.

Figure 7A:
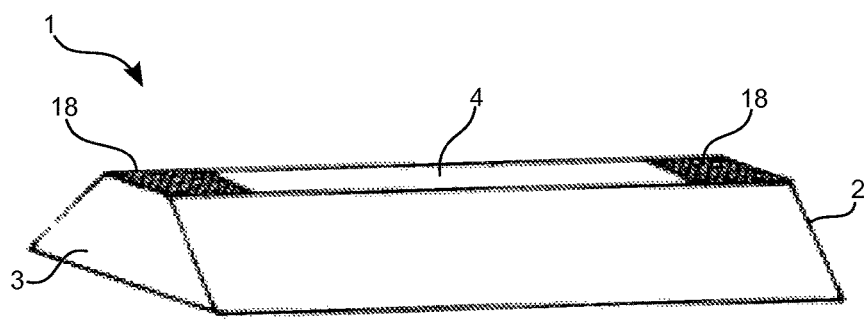
FIG. 7A demonstrates a side perspective view of an embodiment f the present invention.
Figure 7B:
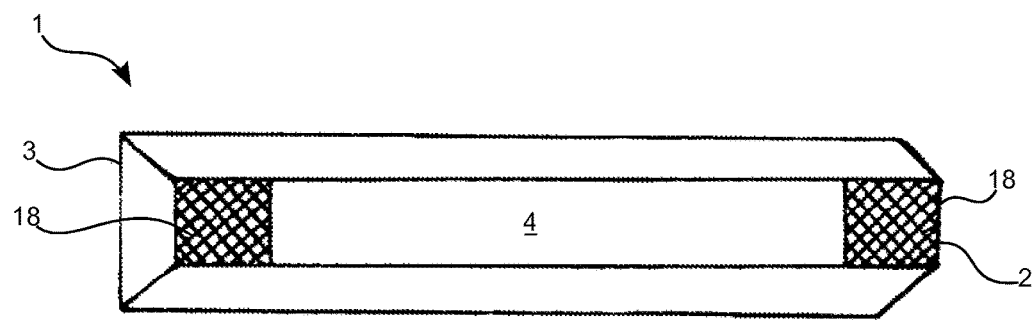
FIG. 7B demonstrates a top perspective view of an embodiment of the present invention.
Figure 7C:
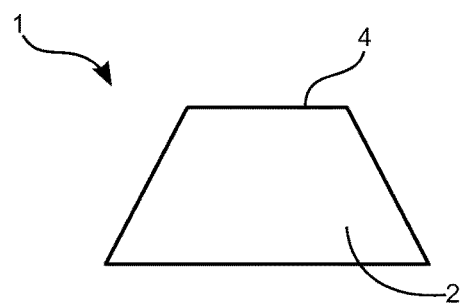
FIG. 7C demonstrates an end view of an embodiment of the present invention.

Referring to FIGS. 7A-C, intergluteal pad 1 may include flat and convex top 4, absent of any lowered or raised features such as concave spaces, cavities, or nubs. Pad 1 may include adhesive 18 to contact patient skin. It is preferable to include adhesive 18 on top 4, towards ends 2 and 3. Adhesives 18 can be applied along intergluteal space on alternative sides of patient anus.

Figure 8A:
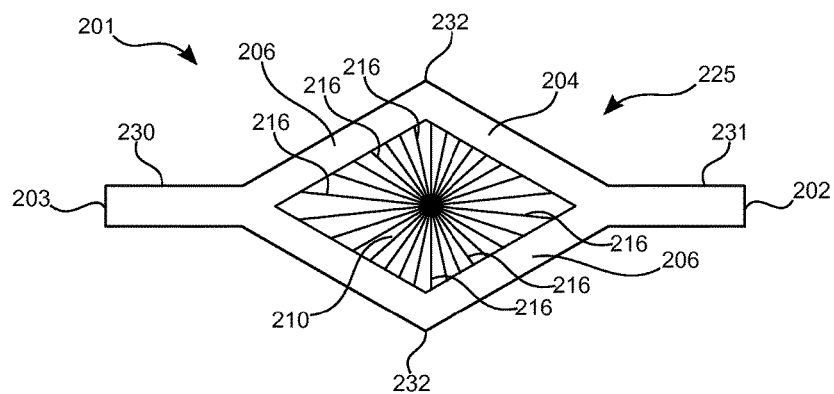
FIG. 8A demonstrates a top view of an embodiment of the present invention.
Figure 8B:
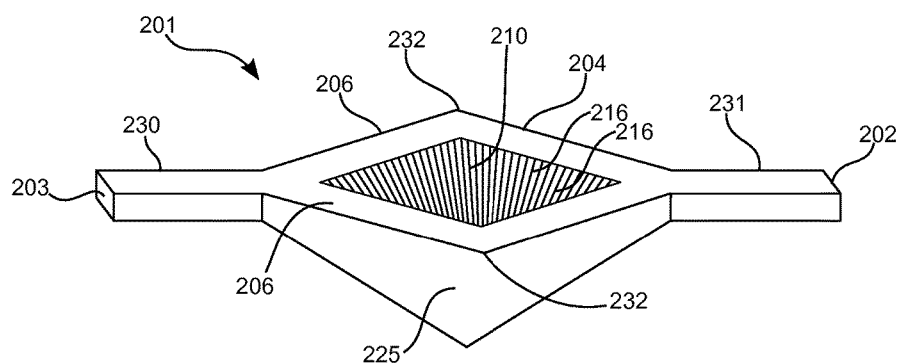
FIG. 8B demonstrates a side perspective view of an embodiment of the present invention.

Referring to FIGS. 8A-B, intergluteal pad 201 may include body 225 with cavity 210. Cavity 210 is defined by border of pressure element 206 along top 204. Preferably, pressure element 206 is sized to surround the anal opening and apply pressure around the external hemorrhoidal plexus, and/or support recessed cavity 210. Body 225 extends to posterior end 203 via posterior post 230, whereby post is adapted to fit between gluteal cheeks. Anterior end 202 includes anterior post 221 to fit ventrally. Posts 230 and 231 may preferably include surface adhesive to affix pad to patient's skin. Adhesive may also or alternatively be applied along pressure element 206. Cavity 210 may include ridges 216 to provide a variegated surface structure. Extending sides 232 provide for a shape that extends wider than posts 230 and 231, to surround features of patient's perianal.

Figure 9A:
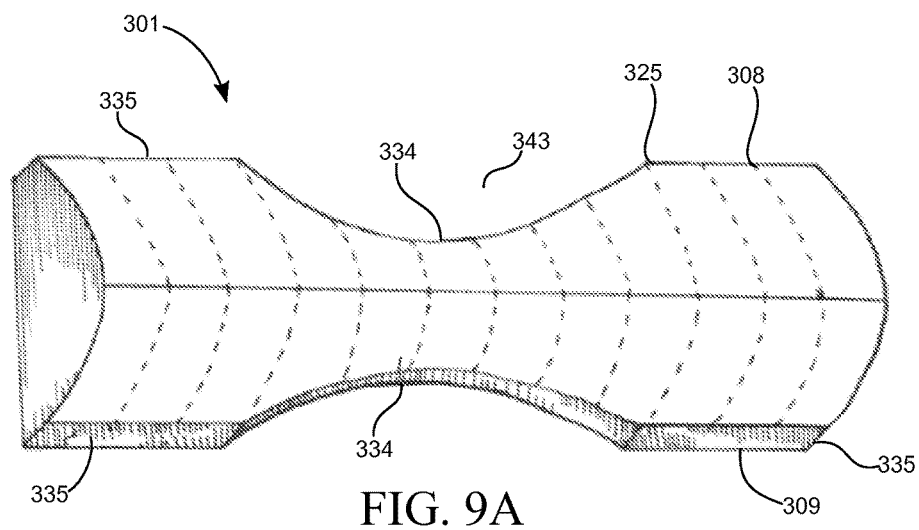
FIG. 9A demonstrates a top view of an embodiment of the present invention.
Figure 9B:
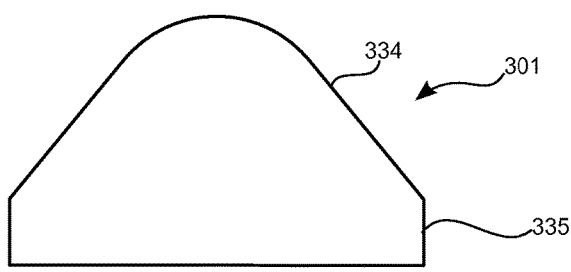
FIG. 9B demonstrates an end view of an embodiment of the present invention.
Figure 9C:
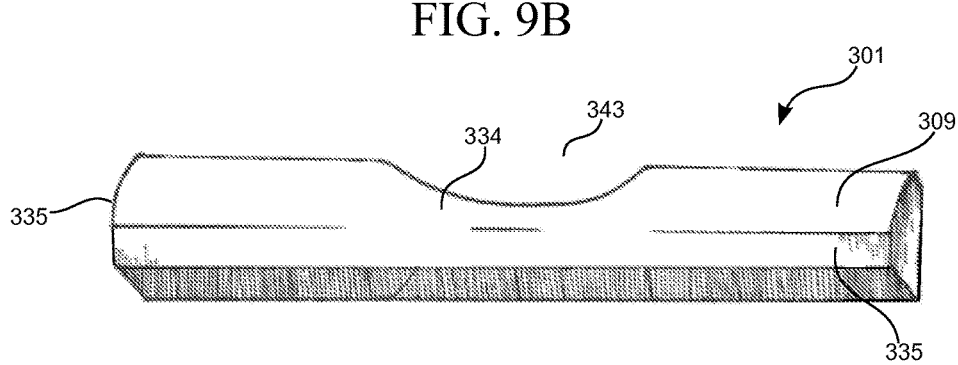
FIG. 9C demonstrates a side view perspective of an embodiment of the present invention.

Referring to FIGS. 9A-C intergluteal pad 301 includes an alternative wishbone shape with wraparound concavity 343 along the center portion of body 325. FIG. 9A includes broken lines to denote contour. Sides 308 and 309 include sloping sides 334 and flat sides 335 providing a shape viewed along the side as shown in FIG. 9B.

Figure 10A:
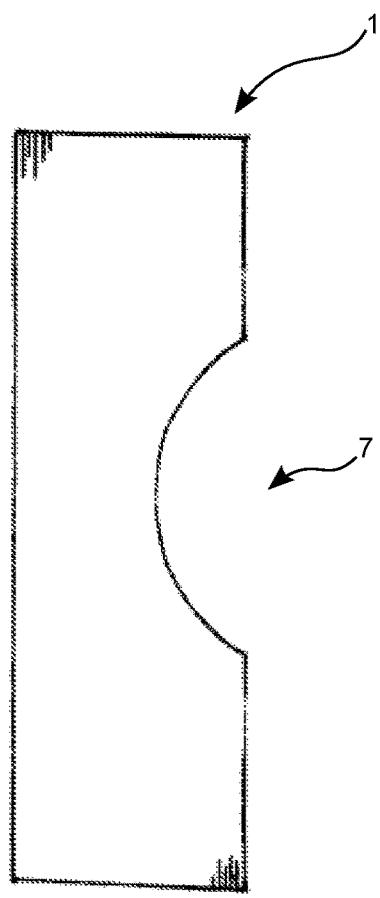
FIG. 10A demonstrates a side view of an embodiment of the present invention.
Figure 10B:
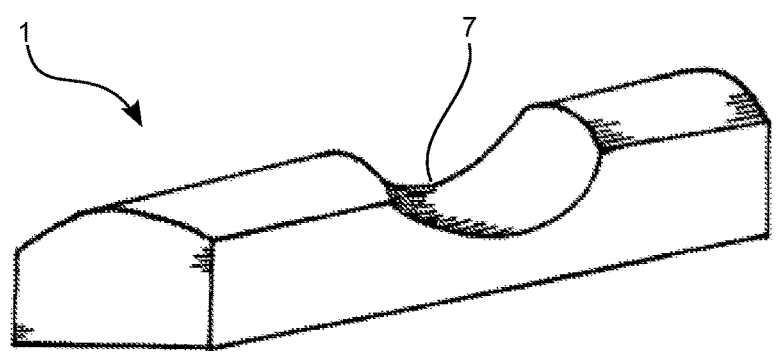
FIG. 10B demonstrates a side perspective view plan embodiment of the present invention.
Figure 11:
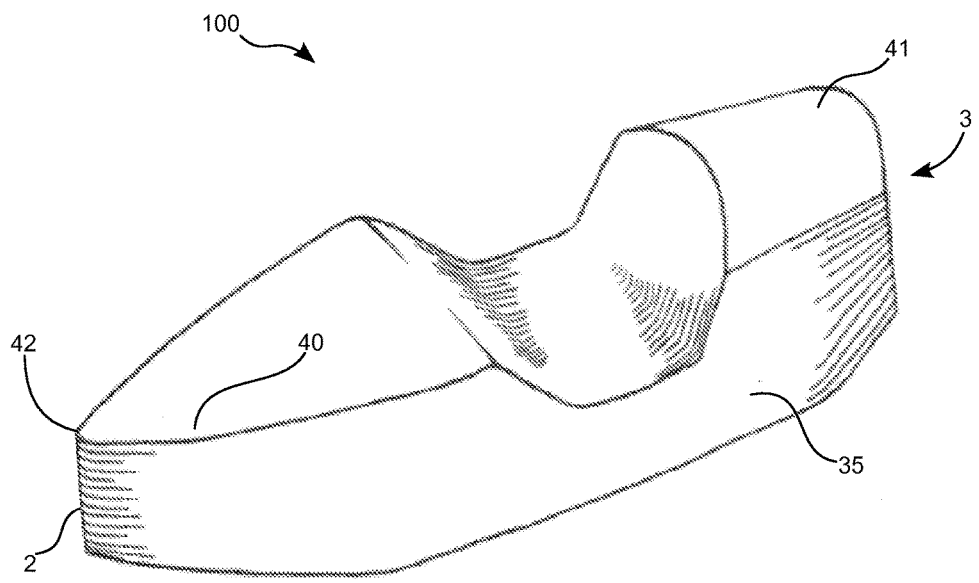
FIG. 11 demonstrates a lateral side perspective view of an embodiment of the present invention.

FIG. 10A and 10B, demonstrate an intergluteal pad 1 with alternative concave section 7 that is rounded to provide gradual pressure relief and remove harsh edges.

Figure 12A:
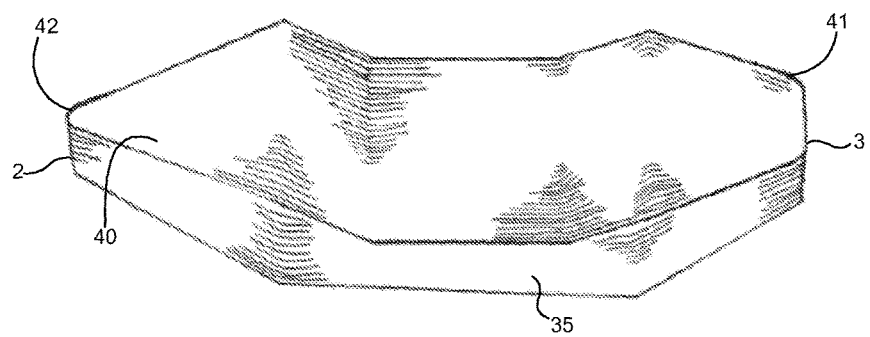
FIG. 12A demonstrates a top view of an embodiment of the present invention.
Figure 12B:
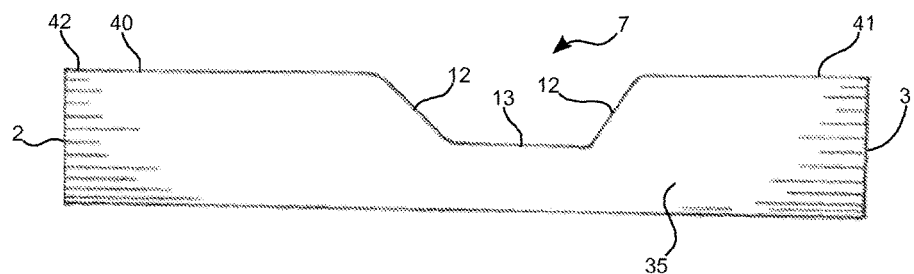
FIG. 12B demonstrates a side view of an embodiment of the present invention.
Figure 12C:
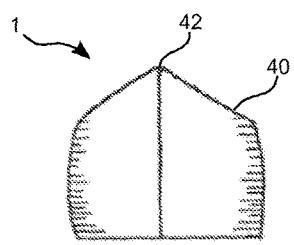
FIG. 12C demonstrates a bottom end view of an embodiment of the present invention.
Figure 12D:
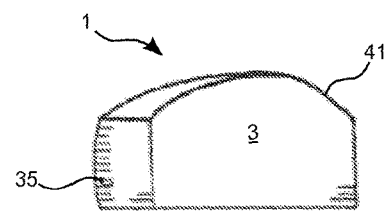
FIG. 12D demonstrates a top end view of an embodiment of the present invention.

As shown in FIGS. 11 and 12A-D, intergluteal pad 1 may include as shape with narrow ends whereby anterior end 2 includes bow 40 and posterior end 3 includes stern 41. Bow 40 narrows to bow edge 42 to make insertion and positioning easier in light of the geometry of the perianal and perineum region. Flat sides 35 may curve to provide appropriate shape to pad 1. As shown in FIG. 12B, concave space is defined by base 13 and walls 12. Walls 12 may be angled off of ninety degrees to provide for a smoother feel.

Figure 13:
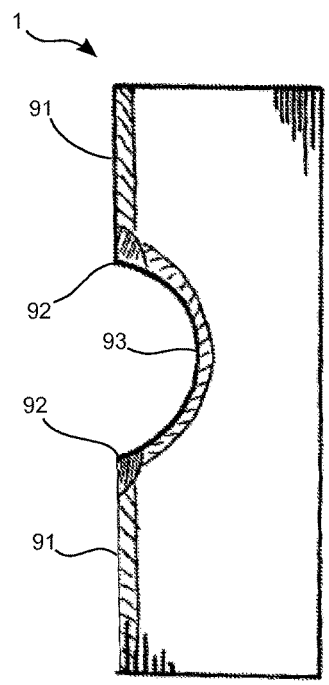
FIG. 13 demonstrates a lateral side view of an embodiment of the present invention.
Figure 14:
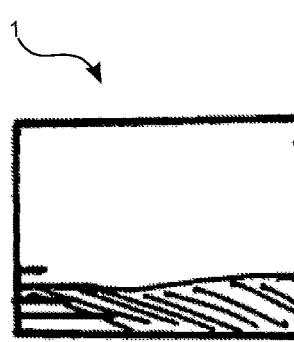
FIG. 14 demonstrates an end view of an embodiment of the present invention.
Figure 15:
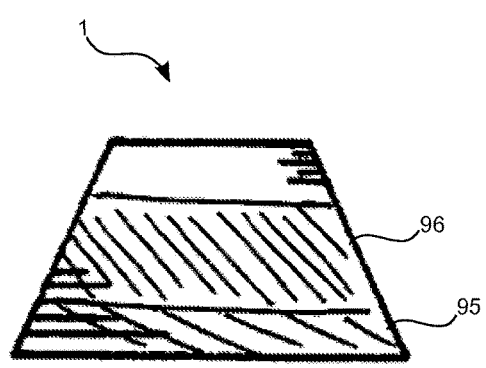
FIG. 15 demonstrates an end view of an embodiment of the present invention.
Figure 16:
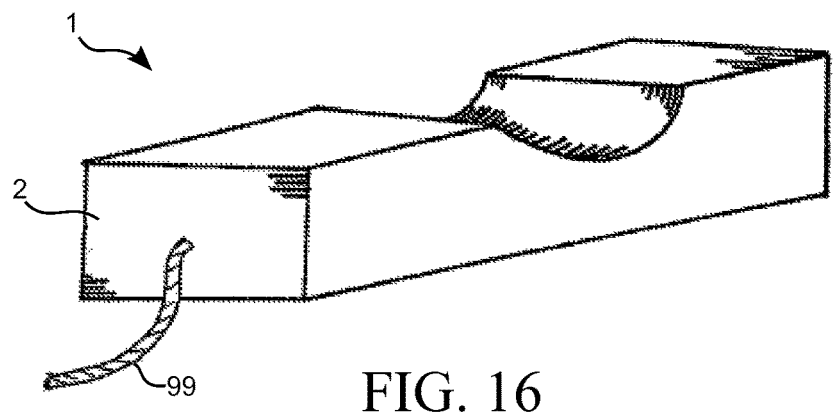
FIG. 16 demonstrates a perspective view of an alternative embodiment of the present invention.
Figure 17:
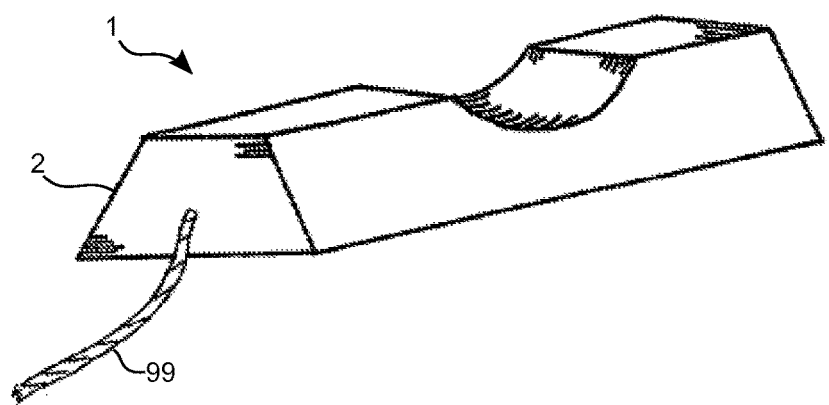
FIG. 17 demonstrates a perspective view of an alternative embodiment of the present invention.

Referring to FIGS. 13-17, intergluteal pad 1 may come in varied forms and shapes, such as rectangular (FIGS. 14 and 16) and trapezoidal (FIGS. 15 and 17).

As shown in FIG. 13, intergluteal pad 1 may include various zones for the inclusion of impregnated therapeutic solutions. Top section 91 may include all or most of the to surface for impregnation of a therapeutic solution around the coddled tissue, or may include anti-inflammatory drugs to reduce swelling. Top section 91 may also include impregnated mild adhesives to secure the product in place. Corners 92 may also provide zones for impregnated therapeutic solutions or adhesives. Cavity zone 93 may include lining which is impregnated with therapeutic solution, particularly when the cavity is placed over swollen or prolapsed tissue to provide steroidal or non-steroidal relief. As such any portion 91, 92 or 93 can also include a variety of similar or dissimilar medications, such as therapeutic solutions, such as pain relief or any solution as described above.

As shown in FIG. 14, backplate 95 may be included in intergluteal pad 1 to provide for support of the pad. Backplate 95 may be made from a stiffer material than the remainder of the pad in order to retain the shape when placed intergluteally. As shown in FIG. 15, backplane 95 may be paired with a standard material zone 96, whereby the standard material zone provide further support to the pad, but not at the expense of the top region for contact with the patients perianal regions or impregnation of solutions. Zone 96 can also be made from a material that prevents impregnated solutions from migrating too far from the top of the pad. Pad 1 may also include an internal matrix/skeleton (not shown) to provide support for the shape of pad 1 when used as a spacer. The matrix may be made of a different material than the pad, one more firm/stiff than cotton, such as plastic, metal, etc.

As shown in FIGS. 16 and 17, pad 1 may include access handle 99, such as a string affixed to ends 2 or 3. Handle 99 allows for easier removal of the pad when emplaced on a user and in need of replacement or removal. Handle 99 may be placed on one or both ends. When the product is symmetric, and the user may determine the most convenient location for the single handle and place it anteriorly or posteriorly. Handle 99 is preferably as cotton string mounted or secured within pad 99 to allow longitudinal and lateral pulling on the handle to exert a force on pad 1 to remove from user. Mounting of handle may be secure enough to overcome adhesive application, in order to remove the pad.

Figure 18A:
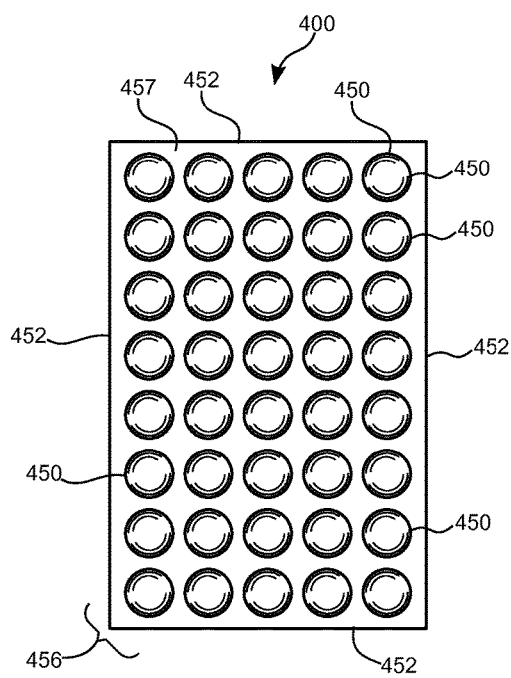
FIG. 18A demonstrates a top view of a cover of the present invention.
Figure 19:
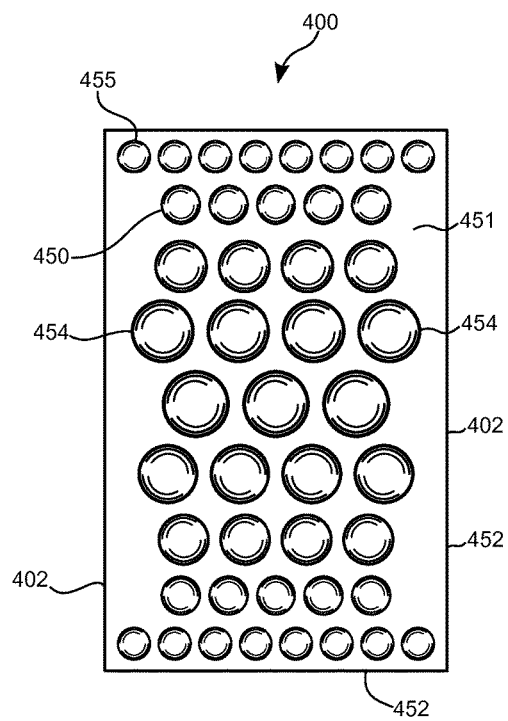
Figure 18B:
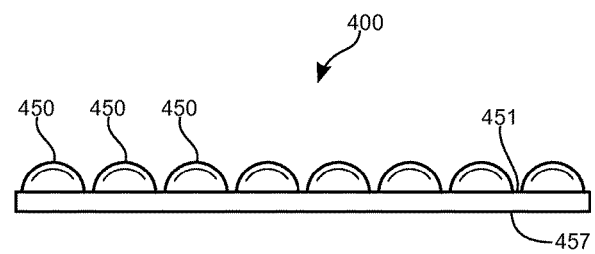
FIG. 18B demonstrates a side view of a cover of an embodiment of the present invention FIG. 19 demonstrates a top view of a cover of the present invention.

FIGS. 18A-B and 19 demonstrate alternative top surface features and an alternative embodiment of the present invention. Roof 400 may include top 451 defined within edges 452. Top 451 provides nodes 450 which act as bosses, or nubs, to apply pressure in specific areas. Nodes 450 may be arranged in an array 456 to provide regular surface pressure features. Alternatively, as shown in FIG. 19, nubs 450 may include large nubs 454 and small nubs 455 to provide alternate pressures. The center 401 preferably includes larger nubs 454 while smaller nubs 455 provide as less pronounced surface towards sides 402. As seen in FIG. 18B, roof 400 may be a thin plane with adhesive plane 457 directly below and opposite nubs 450 on top 451. Roof 400 is to be applied to intergluteal pad (not shown) via adhesive plane 457 to provide a specific pressure surface to the intergluteal pad device. In the alternative, roof 400 may be used directly as a pad to provide selective surface features and pressures and pressure relief. When roof 400 is used in isolation of greater pad as a sort of thinner product, roof 400 is bent in half (with nubs exposed outwardly), and fitted between the gluteal cheeks and perianal. Nubs 450, particularly nubs around outside perimeter, may include surface adhesive to secure roof 400 in place. Nubs, preferably at least one of the larger nubs 454 may encapsulate, or be impregnated with a therapeutic solution for selective application. Nubs may alternatively include a stiff material to help apply pressure or effect manual reduction in prolapse or swollen tissue.

Figure 20:
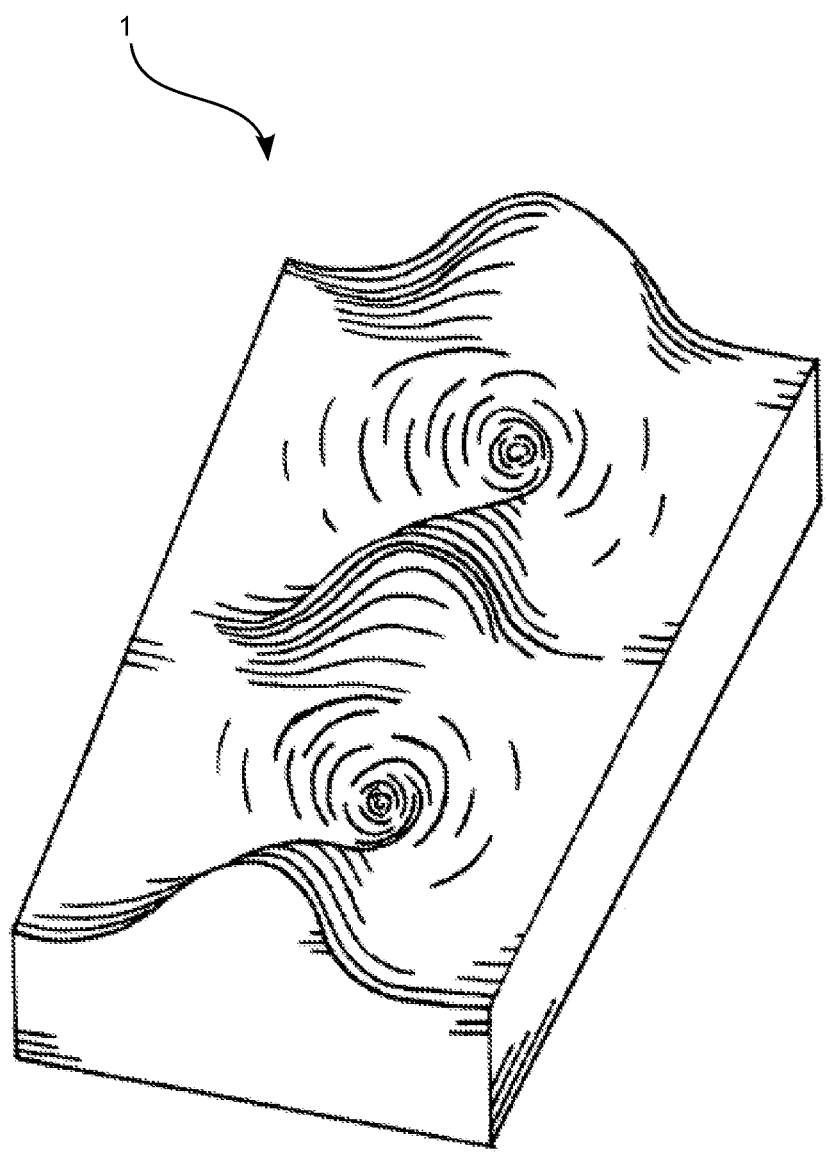
FIG. 20 demonstrates a perspective view of an alternative embodiment of the present invention.
Figure 21:
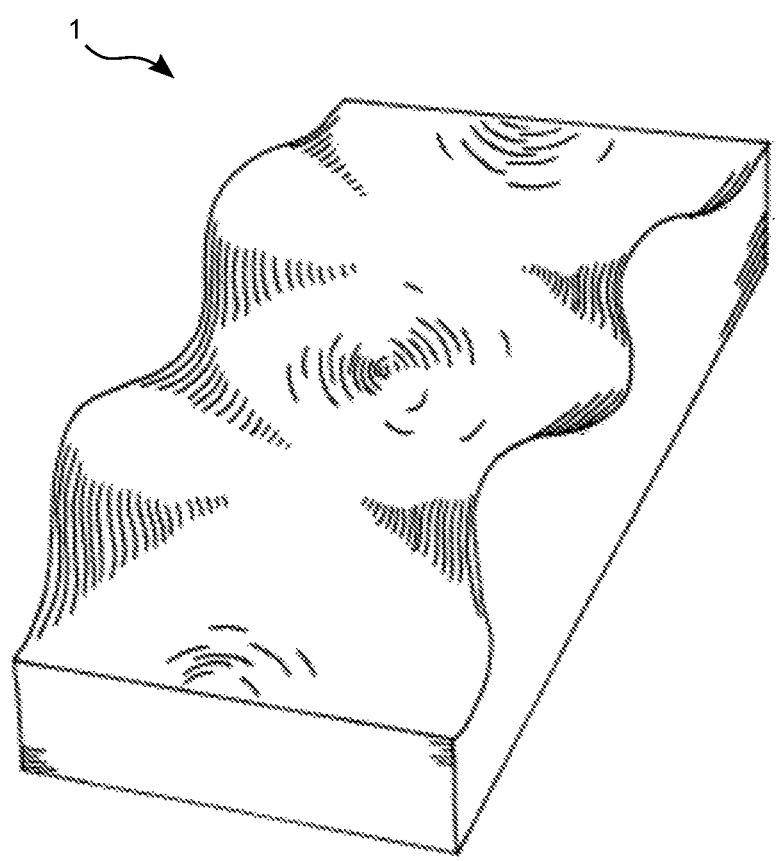
FIG. 21 demonstrates a perspective view of an alternative embodiment of the present invention.
Figure 22:
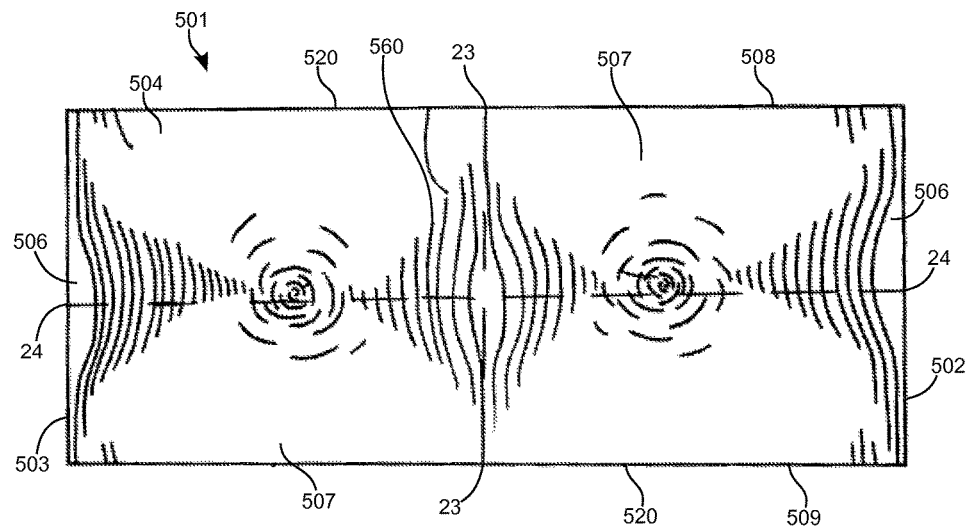
FIG. 22 demonstrates a top view of an embodiment of the present invention.
Figure 23:
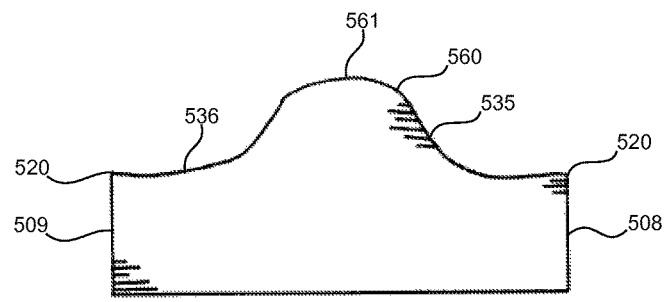
FIG. 23 demonstrates a cross-sectional view along the line 23-23 of FIG. 22.
Figure 24:
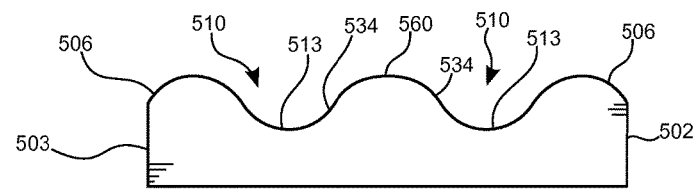
FIG. 24 demonstrates a cross-sectional view along the line 24-24 of FIG. 22.

FIGS. 20 and 21 demonstrate various embodiments of pad 1 that are further detailed in FIGS. 22-24 and FIGS. 25-27 respectively. As shown in FIG. 22, pad 501 includes ends 502 and 503, and sides 508 and 509. Side edges 520 form edge of top 504. Gently sloping concave sections 507 feature on top 504. Pressure elements 506 rise at the ends and pressure feature 560 is centered and includes to lull three hundred-sixty degree mound. Concave sections 507 include cavities 510 falling on sloping sides 534 and base 513. As seen along cross section 23-23 of FIG. 22, FIG. 23 represents a cross-section of FIG. 22. Pressure feature 560 is demonstrated as a mound in profile. Lateral sides 535 and 536 slope from peak 561 to edge 520 at sides 508 and 509. As seen along cross section 24-24 of FIG. 22, FIG. 24 represents a cross-section of FIG. 22. Center mound pressure feature 560 slopes down sides 534 to cavity base 513 between ends 502 and 503. Between center pressure feature 560 and end pressure elements 506, cavities 510 form with base 513 at the bottom.

Figure 25:
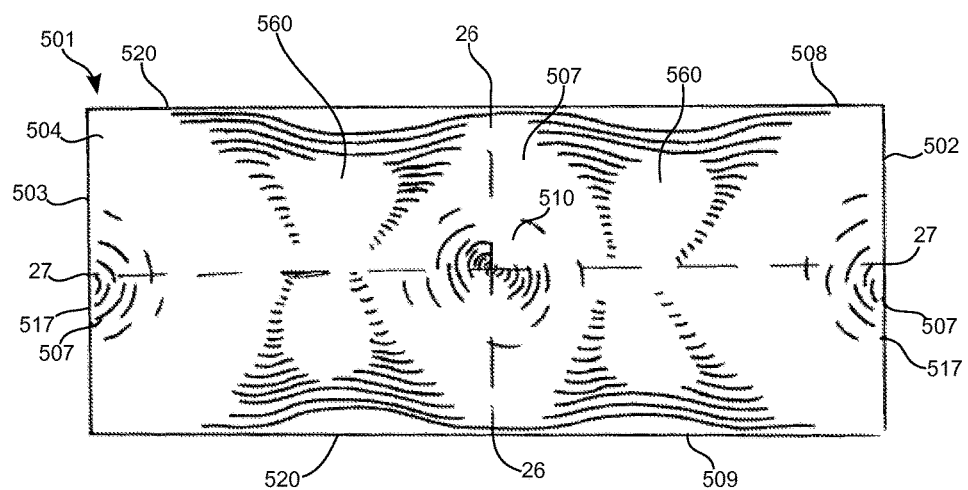
FIG. 25 demonstrates a top view of an embodiment of the present invention.
Figure 26:
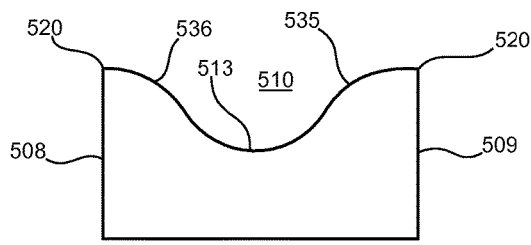
FIG. 26 demonstrates a cross-sectional view along the line 26-26 of FIG. 25.
Figure 27:
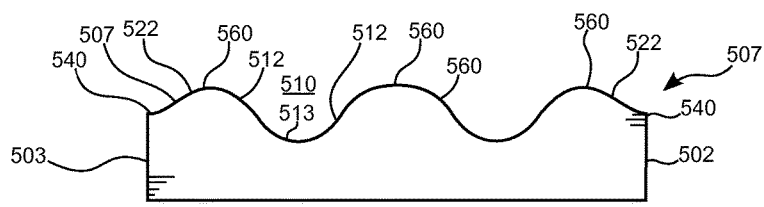
FIG. 27 demonstrates a cross-sectional view along the line 27-27 of FIG. 25.

As shown in FIG. 25, pad 501 includes ends 502 and 503, and sides 508 and 509. Gently sloping concave section 507 features on top 504. Pressure elements 560 rise at either side of central cavity 510. Top 504 is rimmed by edges 520. Ends have partial cavities 517. As seen along cross section 26-26 of FIG. 25, FIG. 26 represents a cross-section of FIG. 25. Center cavity 510 includes base 513 and sloping lateral sides 535 and 536 to edges 520 at sides 508 and 509. As seen along cross section 27-27 of FIG. 25, FIG. 27 represents a cross-section of FIG. 25. Center cavity 510 includes base 513 and sides 512. Separate mounds, or pressure features 560, reside on either end of cavity 510. Pressure elements 560 include outer sides 522 sloping towards ends 502 and 503. Ends also include concave sections 507 with partial cavities 540.

I claim:

1. An intergluteal spacing device for selectively applying and relieving pressure perianally, said device comprising:
    a. an elongated body comprising an anterior end and a posterior end on opposite ends of a longitudinal axis, a right side and a left side, and further comprising a central portion along said longitudinal axis between said anterior end and said posterior end; whereby said intergluteal spacing device is adapted to be placed along a surface of a body of a user whereby the posterior end is positioned posterior said anterior end, and said central portion is adapted to position over at least a part of a user perianal area;
    b. said central portion comprising at least one central concave portion adapted to be placed opposite at least a portion of the user's perianal area, said central concave portion providing at least one central cavity extending across a top surface of the device from the right side to the left side for the adjustment of pressure in and/or around the anus and/or external hemorrhoidal plexus;
    c. at least one pressure element extending across said top surface and adjacent, and anterior said at least one central concave portion, said at least one pressure element on said longitudinal axis; and
    d. a further cavity on said longitudinal axis, said further cavity adjacent and anterior said at least one pressure element.

2. The intergluteal spacing device of claim 1, further comprising a generally trapezoidal cross-sectional shape, said trapezoidal cross-section comprising a wide bottom and a narrow top.

3. The intergluteal spacing device of claim 2, whereby the narrow top comprises said at least one central concave portion.

4. The intergluteal spacing device of claim 1, further comprising at least a second pressure element adjacent and posterior said at least one central concave portion between said anterior end and said posterior end.

5. The intergluteal spacing device of claim 4 further comprising and a second further cavity adjacent and posterior said at least second pressure element.

6. The intergluteal spacing device of claim 1, further comprising a top surface; and an adhesive applied to at least one portion of said top surface for selectively positioning and securing said device.

7. The intergluteal spacing device of claim 1, further comprising a generally convex top between said anterior end and said posterior end, said generally convex top comprising said at least one cavity is positioned centrally along said top.

8. The intergluteal spacing device of claim 1, further comprising at least one nub arranged to selectively apply pressure on at least a portion of the perianal area.

9. The intergluteal spacing device of claim 1, further comprising at least one therapeutic solution.

10. The intergluteal spacing device of claim 9, whereby said therapeutic solution is impregnated within said intergluteal spacer.

11. An intergluteal device for selectively applying and relieving pressure perianally, said device comprising:
    a. an anterior end opposite a posterior end, said anterior end and said posterior end along a longitudinal axis, a right side and a left side along a transversal axis, said intergluteal device adapted to fit interglutealy with said posterior end forward and said anterior end rearward;
    b. a flexible surface comprising at least one nub adapted to apply pressure to a patient's perianal tissue;
    c. at least one central cavity on said longitudinal axis and extending across said transversal axis from said right side to said left side, for selective application of pressure relief;
    d. wherein said nub is positioned adjacent and posterior said at least one central cavity; and
    e. a second cavity posterior said at least one central cavity on said longitudinal axis and extending across said transversal axis from said right side to said left side.

12. The intergluteal device of claim 11 further comprising an outside perimeter, said outside perimeter comprising at least one adhesive affixed to at least a portion of said outside perimeter.

13. The intergluteal device of claim 11, wherein said at least one nub is impregnated with a therapeutic solution.

14. The intergluteal device of claim 11 further comprising a second nub positioned adjacent and anterior said at least one central cavity.

15. The intergluteal device of claim 14 further comprising a second cavity anterior said at least one central cavity on said longitudinal axis.

16. The intergluteal device of claim 11 further comprising a second nub.

* * * * *